May 23, 1972 H. W. MOTZKAU Plant Pat. 3,188
AZALEA PLANT
Filed Sept. 11, 1970
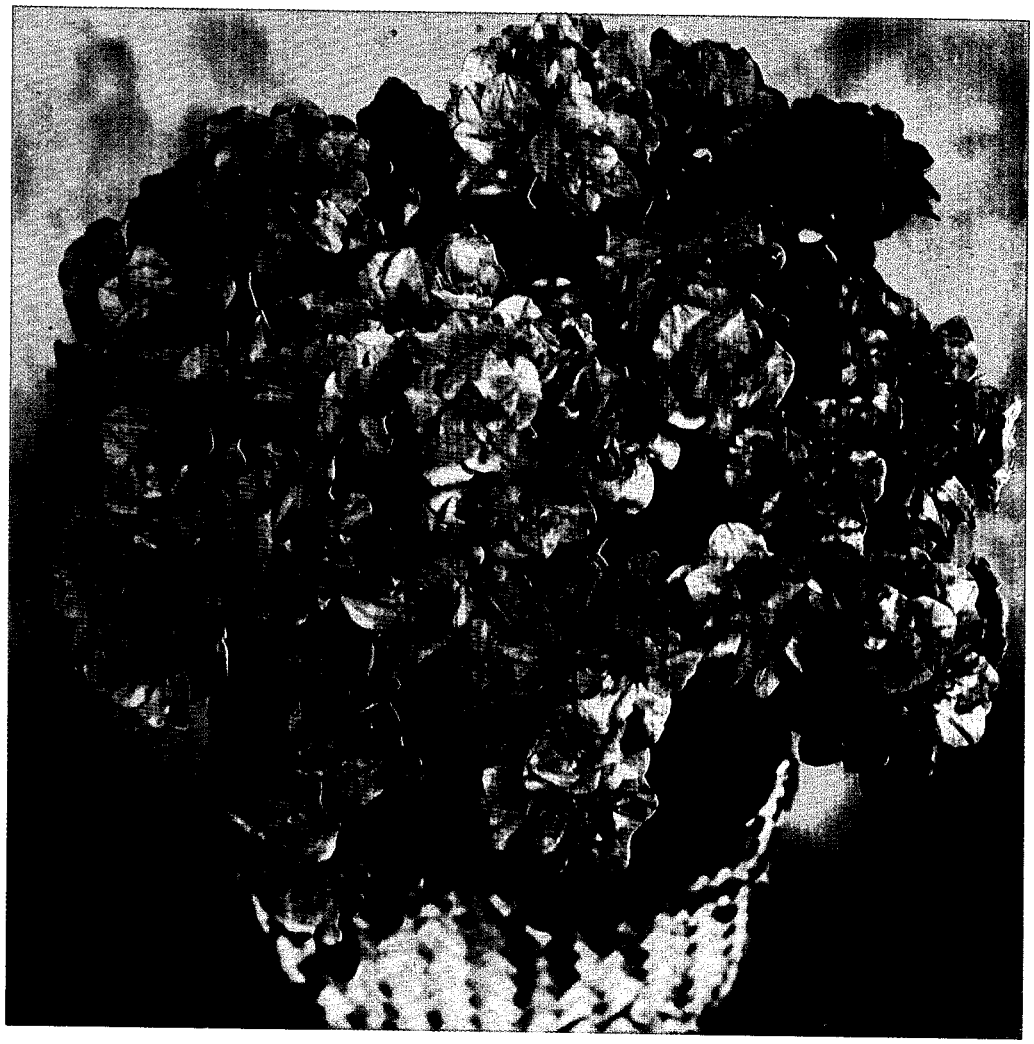
INVENTOR
HENRY W. MOTZKAU
BY
Oberlin, Maky, Donnelly & Renner
ATTORNEYS

United States Patent Office

Plant Pat. 3,188
Patented May 23, 1972

3,188

AZALEA PLANT

Henry W. Motzkau, Whitewater, Wis., assignor to Yoder Brothers, Inc., Barberton, Ohio

Filed Sept. 11, 1970, Ser. No. 71,631
Int. Cl. A01h *5/00*
U.S. Cl. Plt.—57 1 Claim

The present invention comprises a new and distinct variety of azalea plant resulting from crossing certain azalea selections in a program of hybridization. The seed parent is identified in the breeding program as seedling #437 and the pollen parent is identified as seedling #951. Both of these parents are unnamed and unpatened.

The new variety is similar in many respects to Valentine U.S. Plant Patent No. 2492, having the same characteristics as Valentine of rapid growth and semi-upright compact growth habit.

The new variety is distinguished from Valentine by the following characteristics:

(1) The plant finishes 10% larger when grown under the same conditions from equal size liners.

(2) It sets buds and forces more uniformly.

(3) It does not revegetate as readily and does not require as much removal of lateral vegetative growth during the forcing time.

(4) It is recommended for year round flowering while Valentine is recommended only from mid-December through mid-March.

(5) Meadowlark has superior keeping quality as compared to Valentine, keeping approximately one week longer under home conditions.

(6) It has a deep rose color as compared to the red color of Valentine.

The new variety was selected from progeny of seedlings from the above-mentioned parents. Varietal worth was determined by flowering liners built up from the initial selection in a year round and natural season developmental flowering program over a period of 5 years in Ohio. Stock growth was evaluated in the vicinity of Fort Myers, Fla.

My new variety has been asexually reproduced by cuttings at Whitewater, Wis., and has been found to retain its distinctive characteristics through successive propagations.

My new variety when grown in the vicinity of Barberton, Ohio, has a response described as mid-season, and the following detailed description is based on observations made of the new variety in a greenhouse in Barberton, Ohio. The response time and blooming period may vary significantly with varying environmental conditions such as temperature and amount of daylight. Suggested flowering period for natural season is January through April, and for all 12 months in a controlled flowering program for all the United States.

The accompanying drawing shows the new variety as nearly true as possible with a color illustration of this type.

The following is a detailed description of my new variety, the color references being to the Munsell Color Book, 1963 edition. Where meaningful, comparisons have been made with the variety Valentine.

Botanical classification: *Rhododendron hybrida,* evergreen type.

Flower: Spring Color; (May in Ohio).

| | Meadowlark | Valentine |
|---|---|---|
| General tonality | Dark rose 1.25R4/14 | Vivid red between 5R5/13 and 5R5/14. |
| Sepals first divide | Deep rose red 2.5R4/14 | Vivid red 5R5/13. |
| Petals unfurl | Rose between 1.25R4/14 and 2.5R4/14. | Darker than above. |
| Fully open— | | |
| Inside | Rose 1.25R4/14 | Vivid red 5R5/13. |
| Reverse | Dark rose near 2.5R4/14. | Do. |
| Base of petal | Light red near 5R4/10-5R4/12. | |
| Incomplete outer hose. | Dark rose near 2.5R4/14 blending to green 5GY6/8. | |
| Discoloration as ages. | 4-5 weeks deep purplish red 5R3/12-2.5R3/10. | 3rd week—darker and wilts. |

*Summer Color:* (*August in Ohio*).

*General tonality.*—Deep rose red 2.5R4/14.

*Sepals first divide.*—Deep red 2.5R3/10.

*Petals unfurl.*—Deep rose red 2.5R4/10.

*Fully open.*—Inside—deep rose red 2.5R4/14; reverse—deep rose red 2.5R4/14; base of petal—light red 5R4/12; incomplete outer hose—rose 1.25R4/14 blending to green 5GY6/8.

*Fall-Winter Color:* (Barberton, Ohio).

*General tonality.*—Rose, 7.5RP5/12.

*Sepals first open.*—Dark rose, 10RP4/14.

*Petals unfurl.*—Rose near 8.75RP4/12.

*Fully open.*—Inside—rose, 7.5RP5/12; Outside—rose near 8.75RP4/12; base of petal—light red, 5R4/10; incomplete outer hose—rose near 8.75RP4/12 blend to green 5GY6/8.

*Bud.*—Size—medium; form—conical; opening habit—cup-like; retains cup-like form.

*Bloom.*—Size—medium; average—2½"; range 2"–3"; borne—several together in clusters: average 4, range 2–7; form—semi-double with varying degrees of petaloid stamens; calyx of individual flowers are petaloid to varying degrees; (Valentine form: semi-single, hose in hose).

*Blooming habit.*—Once, profusely; response—natural season; mid-season year round; mid-season timing, all 12 months; sepals—fine toothed; peduncle—length, short; aspect, hairy; strength, strong.

*Petals.*—Texture—soft; appearance—smooth; inside, satiny; outside, satiny; form—rounded, notched; arrangement—imbricate with petaloids present; fragrance—none; persistence—long average life in home (in excess of 4 weeks); non-shatter; longevity—greenhouse, 3–4 weeks; home 4–5 weeks.

*Reproductive organs.*—Stamen anthers—large, many petaloid, generally less than 5, color reddish pink 7.5RP2/4–7.5RP3/4; filaments—long, color light red 5R4/12; style—columnar, medium length, rather thin, pink 10RR4/10; stigmas—normal, color reddish tan 10R4/6–10R4/14; ovaries—hypogynous.

Plant:

*Bush.*—Growth habit—compact, semi-upright; breaking habit—vigorous, semi-upright; size of average finished product grown from the standard #7 liner of Yoder Brothers, Inc., Barberton, Ohio: height—10"–12"; diameter—10"–15"; budding ease—good under wide variation of environmental conditions; uniformity of budding—good; growth regulator—not needed; rooting habit—good, easy from own roots; vigorous.

*Foliage.*—Leaflets—single; size—length, 2"–3"; average 2½"; width, ½–1½"; average 1"; shape—ovate to obovate– texture—upper, flat; lower, flat; rib and veins—slightly depressed; edge—smooth.

| | Meadowlark | Valentine |
|---|---|---|
| Color: | | |
| New foliage— | | |
| Upper | Light green 7.5GY5/6 | Light green 7.5GY6/8 to 7.5GY5/7. |
| Lower | Light yellow green 7.5GY6/4. | Light green 10GY6/9 to 10GY5/8. |
| Mature foliage— | | |
| Upper | Dark green 7.5GY3/4 | |
| Lower | Green 7.5GY5/4 | |
| Petiole, short | Light green 5GY7/6 | |
| Stems: | | |
| Color— | | |
| New wood | Reddish green 5R4/6 | Light green 7.5GY6/9. |
| Mature wood | Light brown 5RY4/6 | |

*Recommended flowering period.*—Natural season—early January through April; year round—all 12 months in controlled progress.

*Responsiveness to day length and temperature.*—Buds and flowers under a wide range of conditions.

*Resistance to Cylindrocladium*—No apparent sensitivity.

*Cooler tolerance.*—Good, color retention excellent.

*Shipping tolerance.*—Good.

I claim:

1. A new and distinct variety of azalea characterized particularly by its rapid growth, its unique color habit of intensifying its color during the high light periods of the year, its habit of bearing flowers in clusters, its trait of superior keeping quality under home conditions, its non-shattering, its mid-season profuse flowering, its adaptability to year round flowering programs, its evergreen type foliage, its ability to perform under sub-optimum growing conditions, and the ability of its leaves to withstand crowding and long term cold storage without turning yellow or dropping off the plant.

No references cited.

ROBERT E. BAGWILL, Primary Examiner

UNITED STATES PATENT OFFICE
CERTIFICATE OF CORRECTION

Patent No. PP-3,188 Dated May 23, 1972

Inventor(s) HENRY W. MOTZKAU

It is certified that error appears in the above-identified patent and that said Letters Patent are hereby corrected as shown below:

In column 2, line 56, "10RR4/10" should be changed to --10RP4/10--.

In column 3, line 22, "progress" should be --programs--.

Signed and sealed this 2nd day of October 1973.

(SEAL)
Attest:

EDWARD M.FLETCHER,JR.
Attesting Officer

RENE D. TEGTMEYER
Acting Commissioner of Patents